United States Patent
Kunos et al.

(10) Patent No.: US 6,563,009 B1
(45) Date of Patent: May 13, 2003

(54) VASODILATOR CANNABINOID ANALOGS

(75) Inventors: George Kunos, Bethesda, MD (US); Billy Martin, Richmond, VA (US); Raj Razdan, Gloucester, MA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 10/009,813

(22) PCT Filed: Jul. 12, 2000

(86) PCT No.: PCT/US00/01892
§ 371 (c)(1),
(2), (4) Date: Mar. 8, 2002

(87) PCT Pub. No.: WO01/03690
PCT Pub. Date: Jan. 18, 2001

Related U.S. Application Data

(60) Provisional application No. 60/174,381, filed on Jan. 4, 2000, and provisional application No. 60/142,958, filed on Jul. 12, 1999.

(51) Int. Cl.$^7$ .............................................. C07C 39/17
(52) U.S. Cl. ....................... 568/743; 514/729
(58) Field of Search ........................... 568/743; 514/729

(56) References Cited

U.S. PATENT DOCUMENTS

| | | | |
|---|---|---|---|
| 4,025,516 A | | 5/1977 | Razdan et al. |
| 4,116,979 A | * | 9/1978 | Razdan et al. |
| 5,939,429 A | | 8/1999 | Kunos et al. |
| 6,274,635 B1 | * | 8/2001 | Travis |

FOREIGN PATENT DOCUMENTS

WO    WO 99/53917    10/1999

OTHER PUBLICATIONS

Srebnik, J. Chem. Soc., Perkin Trans, I, pp. 1423—1427 (1987).*
Vree, J. Chromatogr., vol. 74, pp. 209–224 (1972).*
Adams, Experienta, vol. 33, pp. 1205–1204 (1997).*
Usami, Chem. Pharm. Bull., vol. 47, pp. 1641–1645 (Nov. 1999).*
Baek, J. Korean Chem. Soc., vol. 35, pp. 59–63 (1991).*
Baek, S. et al., "Boron Trifluoride Etherate on Alumina —A Modified Lewis Acid Reagent. An Improved Synthesis of Cannabidiol.", Tetraheron Letters, 1985, vol. 26, No. 8, pp. 1083–1086.
Rhee, M. et al., "Cannabinol Derivatives: Binding to Cannabinoid Receptors and Inhibition of Adenylylcyclase", J. Med. Chem., 1997, vol. 40, pp. 3228–3233.

* cited by examiner

Primary Examiner—Michael L. Shippen
(74) Attorney, Agent, or Firm—Whitham, Curtis & Christofferson, P.C.

(57) ABSTRACT

Cannabinoids have been found to have antioxidant properties, unrelated to NMDA receptor antagonism. This new found property makes the cannabinoids useful in the treatment and prophylaxis of wide variety of oxidation associated diseases, such as ischemic, age-related, inflammatory and autoimmune diseases. The cannabinoids are found to have particular application as neuroprotuctants, for example in limiting neurological damage following ischemic insults, such as stroke and trauma, or in the treatment of neurodegenerative diseases, such as Alzheimer's disease, Parkinson's disease and HIV dementia. Nonpsychoactive cannabinoids, such as cannabidoil, are particularly advantageous to use because they avoid toxicity that is encountered with psychoactive cannabinoids at high doses useful in the method of the present invention. A particular disclosed class of cannabinoids useful as neuroprotective antioxidants is formula (I) wherein the R group is independently selected from the group consisting of H, $CH_3$, and $COCH_3$

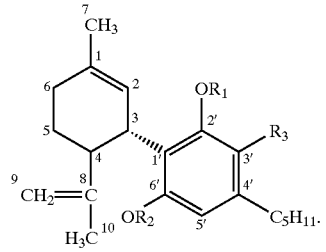

(I)

11 Claims, 2 Drawing Sheets

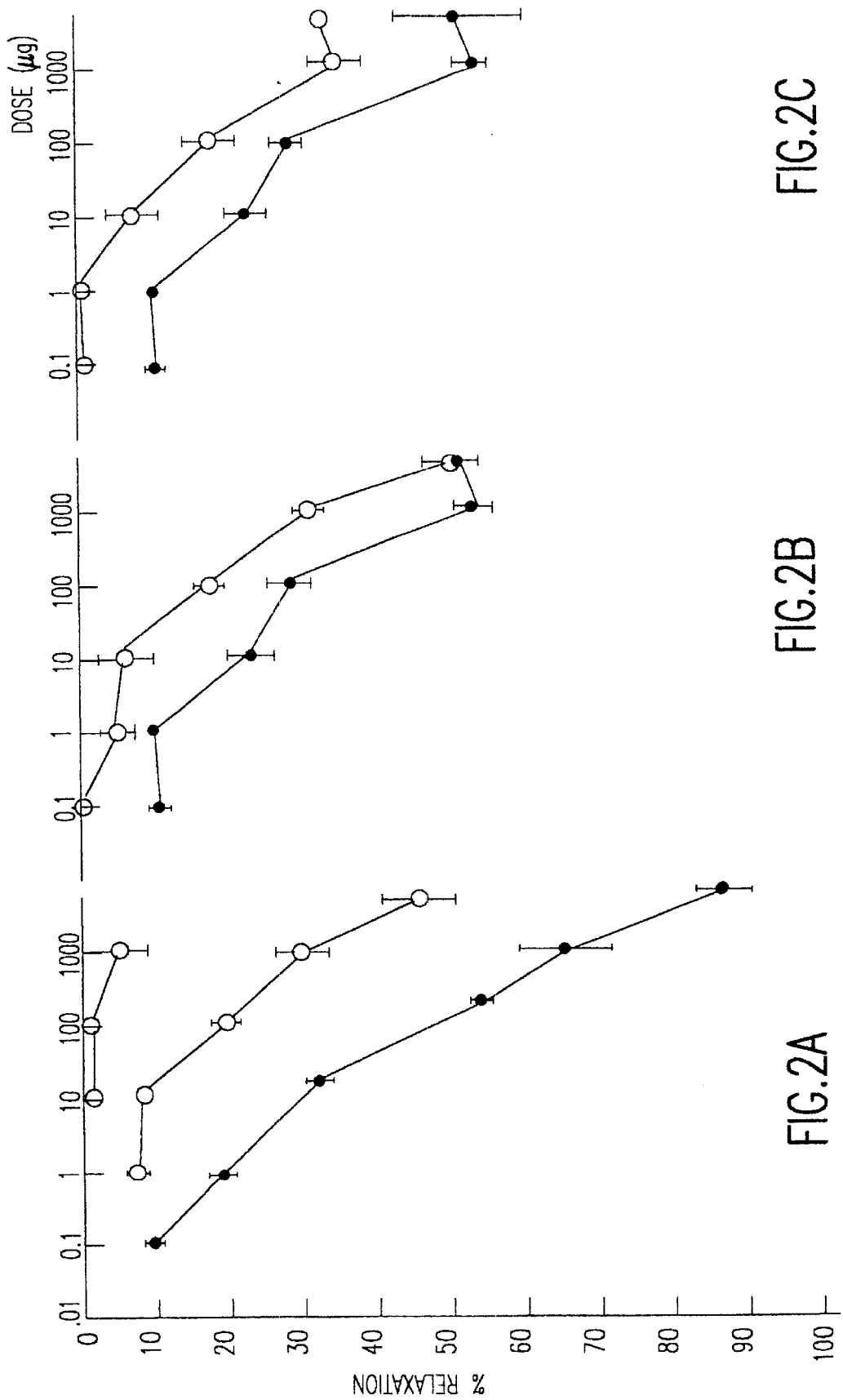

VASODILATOR CANNABINOID ANALOGS

This application is a 371 of PCT/US00/18921 Jul. 12, 2000 which claim benefit of Ser. No. 60/142,958 filed Jul. 12, 2000 and claim benefit of Ser. No. 60/174,381 filed Jan. 14, 2000.

BACKGROUND OF THE INVENTION

FIELD OF THE INVENTION

The present invention relates to the discovery of novel ligands specific for a receptor from the cannabinoid (CB) receptor family. The invention discloses the discovery of novel ligands specific to this receptor that act as antagonists to the natural ligands for this receptor. The invention also relates to the discovery of novel ligands that act as agonists to the natural ligands for this receptor.

The present invention generally relates to ligands of the mammalian CB receptor family and, more particularly, to cannabidiol and abnormal cannabidiol derivatives that act as antagonists and agonists for non CB1 and non CB2 receptor subgoups and to using these derivatives to treat pathological states arising from abnormal vasoconstriction, blood pressure, and heart rate. The ligands of the present invention elicit beneficial pharmacological effects associated with cannabinoid receptor stimulation without the concomitant psychoactive effects associated with previously described cannabinoid receptor family ligands. Accordingly, the compounds of the present invention provide useful pharmacologic compounds which may be administered to treat various disease states without the deleterious side effects associated with previous cannabinoid receptor compounds. The invention thus also relates to methods for the treatment of disease states which may be alleviated by drug-induced vasodilation such as, e.g., high blood pressure, hypertension, coronary artery disease, and peripheral vascular disease. Additionally, the compounds of the present invention may be utilized in labeled and unlabelled form to identify the non CB1 and non CB2 receptors that are the molecular site(s) of action of these compounds and the parental cannabinoid and abnormal cannabinoid ligands.

BACKGROUND DESCRIPTION

Marijuana is a popular recreational drug of abuse because of its psychoactive properties. The major constituent of marijuana is the cannabinoid Δ9-trahydrocannabinol (THC). Naturally occurring cannabinoids may be divided into two categories, plant-derived and endogenous. Plant-derived cannabinoids are known to elicit dramatic psychobehavioral effects and are also known to have complex cardiovascular effects, a prominent component of which is hypotension (Vollmer et al. J. Pharm. Pharmacol. 1974, 26:186–198). Endogenous cannabinoids (endocannabinoids) are a class of lipid-like molecules that share receptor binding sites with plant-derived cannabinoids and mimic many of their neurobehavioral effects (Mechoulam et al. Adv. Exp. Bio. Med. 1996, 402:95–101). Two endocannabinoids have been characterized in some detail: arachidonyl ethanolamide (anandamide) (Devane et al. Science 1992, 258:1946–1949; Felder et al. Proc. Natl. Acad. Sci. USA. 1993, 90:7656–7660) and 2-arachidonyl glyceride (2-AG) (Mechoulam et al. Biochem. Pharmacol 1995, 50:83–90). Like plant-derived cannabinoids, both anandamine and 2-AG are capable of eliciting hypotension (Varga et al. FASEB J. 1998, 12:1035–1044; Varga et al. Eur. J. Pharmacol. 1995, 278:279–283; Stein et al. Br. J. Pharmacol. 1996, 119:107–114; Varga et al. Hypertension 1996, 28:682–688; Lake et al. Hypertension 1997, 29:1204–1210; Calignano et al. Eur. J. Pharmacol. 1997, 337: R1–R2).

Cannabanoids exert their effects by binding to specific receptors located in the cell membrane. To date, two cannabinoid receptors have been cloned, the CB1 receptor expressed primarily in the brain (Matsuda et al. Nature 1990, 346:561–564) but also in some peripheral tissues (Shire et al. J. Biol. Chem. 1995, 270:3726–3731), and CB2 receptors expressed by cells of the immune system (Munro et al. Nature 1993, 365:61–65). Studies with the selective CB1 receptor antagonist SR141716A implicated the CB1 receptor subtype in cannabinoid-induced hypotension and bradycardia (Varga et al. (1995), Eur. J. Pharmacol. 278, 279–283; Lake et al. (1997) J. Pharmacol. Exp. Ther. 281, 1030–1037), a conclusion recently confirmed by the use of mice deficient in CB1 receptors (Ledent et al. (1999) Science 283, 401–404). However, it has recently been reported that in the rat isolated mesenteric arterial bed anandamide elicits prolonged vasodilation partially inhibited by SR141716A, but THC and synthetic agonists highly potent at both CB1 and CB2 receptors, such as HU-210 (17) or WIN 55212-2 (18), do not have a vasodilator effect (Wagner, et al. (1999) Hypotension 33(II);429–434). These findings implicate as-yet unidentified receptor(s) in anandamide-induced mesenteric vasodilation which may be called "CB1-like" receptor(s).

Recent findings indicate that the compound "abnormal cannabidiol" (Abn-cbd) may be a selective agonist of CB1-like receptors that does not interact with CB1 receptors (Adams et al., Experientia 1977, 33:1204–1205, see also U.S. Pat. No. 5,939,429, which are incorporated herein by reference). In both anesthetized rats and mice, 10 mg/kg (i.v.) of Abn-cbd was found to cause hypotension that could be prevented by pretreatment of the animals with 3 mg/kg SR141716A. Abn-cbd elicited similar although shorter lasting hypotension, inhibited by SR141716A, in CB1 receptor knockout −/−mice. Furthermore, in the perfused rat mesenteric vascular bed preparation (in which potent CB1 agonists were found to be inactive), Abn-cbd caused vasodilation which could be inhibited by SR141716A. These last two findings indicate that Abn-cbd induces hypotension via "CB1-like" (non-CB1) cannabinoid receptors. In other experiments it was found that Abn-cbd in doses up to 60 mg/kg does not cause marijuana-like neurobehavioral effects in mice. Furthermore, using an in vitro ligand binding assay Abn-cbd at concentrations up to 100 uM failed to displace a potent known ligand of CB1 receptors from CB1 cannabinoid receptors in a rat brain plasma membrane preparation. These latter findings indicate that Abn-cbd is not an agonist of CB1 receptors. Additional studies have since shown that the vasodilatory effects associated with Abn-cbd are not mediated via binding to CB2 receptors.

In sum, it has been thus far demonstrated that Abn-cbd does not bind to the brain cannabinoid (CB1) receptor and does not elicit cannabinoid-like neurobehavioral effects in rats and mice. However, abn-cbd has been found to lower blood pressure and to dilate isolated mesenteric arteries in normal rats and mice and also in genetically altered mice that do not express CB1 receptors (CB1 knockout mice), or mice that do not express either the CB1 or the CB2 receptor (CB1/CB2 double knockout mice). (Proceedings of the National Academy of Sciences [PNAS], vol. 96, pp. 14136–14142 (1999), which is herein incorporated by reference.). Furthermore, cannabidiol (the parent compound of abn-cbd), which is also devoid of neurobehavioral effects and does not bind to CB1 receptors, does not elicit mesenteric vasodilation but is able to antagonize the vasodilator effect of Abn-cbd (Id. and U.S. Pat. No. 5,939,429).

The vasodilator response to Abn-cbd remains unchanged in the presence of 100 $\mu$M NG-nitro-L-arginine methyl ester (L-NAME) and 10 $\mu$M indomethacin in the perfusion buffer, which indicates that endothelial NO and cyclooxygenase products such as prostacyclin do not contribute to the response. Also, in the presence of 5 $\mu$M capsazepine (Kd at vanilloid VRI receptors: 285 nM), the bolus injection of 4 mg Abn-cbd elicited the same long lasting vasodilation as in its absence. This observation further indicates that inhibition of vasodilation by the Abn-cbd is not attributable to non-specific blockade of vanilloid receptors.

These findings suggest that Abn-cbd and cannabidiol are a selective agonist and antagonist, respectively, of an as yet unidentified cannabinoid-like receptor distinct from CB1 or CB2 receptors. These findings also suggest that agonists of these receptors, such as Abn-cbd, might be useful in the treatment of diseases where drug-induced vasodilation is desirable (e.g. high blood pressure disease or hypertension, coronary artery disease, peripheral vascular disease, abnormal heart rate). The potential usefulness of Abn-cbd may be limited, however, by its relatively low potency, i.e. the need for relatively high doses to elicit vasodilation or to lower blood pressure. Similarly, the inhibitory potency of cannabidiol is also low.

There thus exists a need for analogs of Abn-cbd and cannabidiol that can elicit similar biological activities in smaller doses and thus having a greater potential efficacy in the treatment of pathological states which may benefit from drug-induced regulation of vasodilation.

SUMMARY OF THE INVENTION

It is therefore an object of the invention to provide structurally modified analogs of Abn-cbd, with the aim of obtaining compounds with a similar activity profile, but greater potency than Abn-cbd.

It is another object of the invention to provide methods for the stimulation of mesenteric vasodilation by administering to an animal structurally modified analogs of Abn-cbd.

It is another object of the invention to provide methods for the treatment of pathological states by the administration of analogs of Abn-cbd with a concurrent increase in vasodilation yet without psychoactive side effects.

It is another object of the invention to provide structural analogs of cannabidiol with the aim of obtaining compounds with a similar activity profile, but greater potency than cannabidiol yet without psychoactive side effects.

It is another object of the invention to provide methods for the inhibition of mesenteric vasodilation by administering to an animal structurally modified analogs of cannabidiol.

It is another object of the invention to provide methods for the treatment of pathological states by the administration of analogs of cannabidiol and a concurrent inhibition of vasodilation without psychoactive side effects.

It is another object of the invention to provide methods for the treatment of pathological states by the administration of analogs of cannabidiol and Abn-cbd wherein the pathological states include abnormal blood pressure and abnormal heart rate.

It is yet another object of the invention to provide labeled and unlabelled agonists and antagonists that are specific for a non-CB1 and non-CB2 receptors which may be used as tools to characterize and isolate "CB1-like" receptors that regulate mesenteric vasodilation in animals.

According to the invention, derivatives of cannabidiol and abnormal cannabidiol are provided which act as agonists or antagonists to cannabidiol or abnormal cannabidiol. The compounds of the present invention are provided as derivatives of Abn-cbd and cannabidiol. They are provided in pharmacologically useful compositions and may be used to regulate mesenteric vasoconstriction, blood pressure, and heart rate through ligand-receptor interaction with CB1-like receptors without a concurrent psychoactive effect.

BRIEF DESCRIPTION OF THE DRAWINGS

The foregoing and other objects, aspects and advantages will be better understood from the following detailed description of a preferred embodiment of the invention with reference to the drawings, in which:

FIGS. 2A–C are graphical representation of the effects of various cannabidiol derivative compounds on the vasodilation caused by Abn-cbd derivatives.

DETAILED DESCRIPTION OF THE PREFERRED EMBODIMENTS OF THE INVENTION

Figure 1:
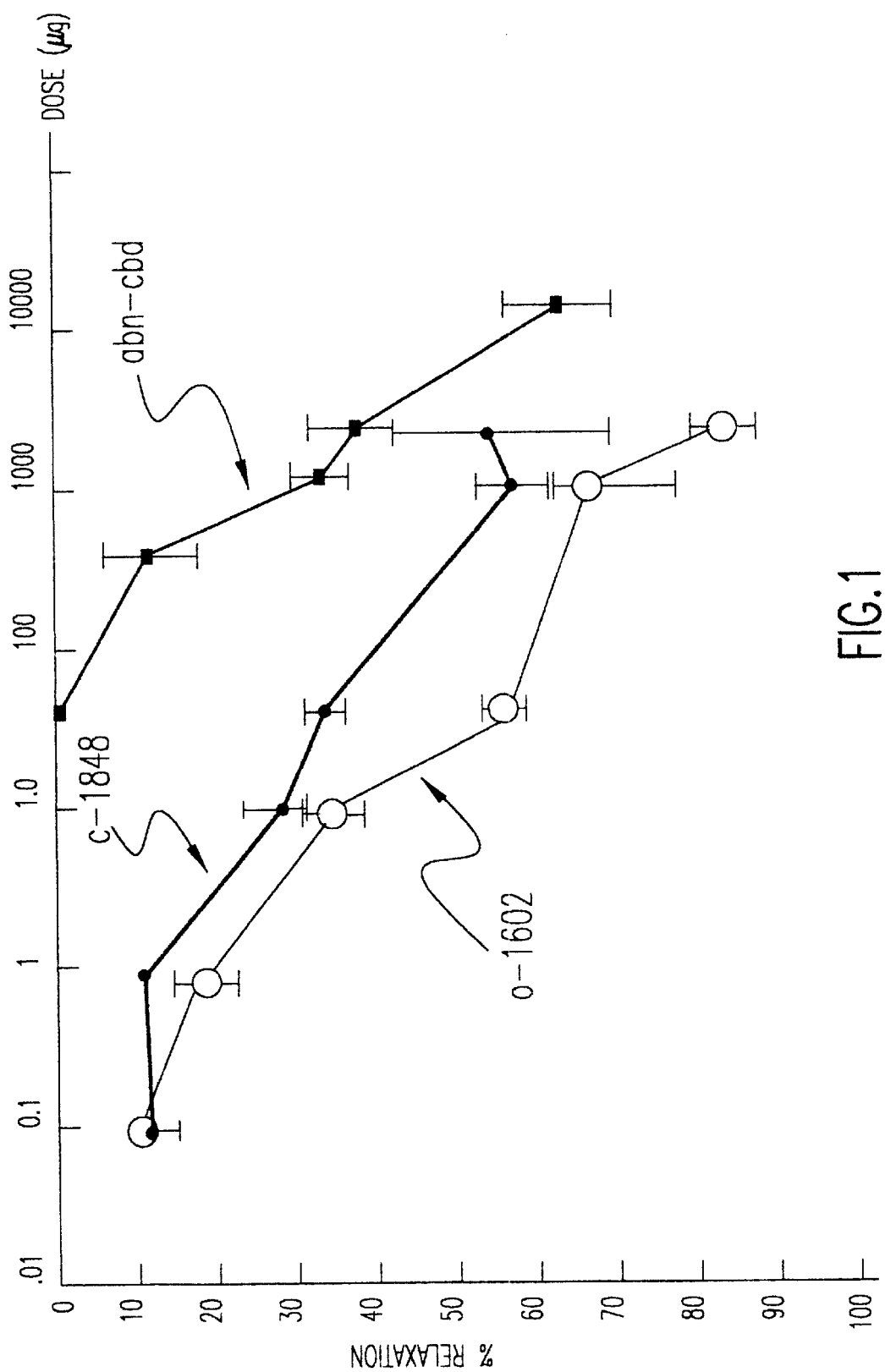
FIG. 1 is a graphical representation of the influence of Abn-cbd and its derivatives on vasodilation on mesenteric vascular tone in mice.

The ability of the compounds of the present invention to mimic some of the actions of the cannabinoids makes them useful for preventing or reversing the symptoms that can be treated with cannabis, some of its derivatives and synthetic cannabinoids in a human subject. Thus, compounds of the invention are useful to treat, prevent, or ameliorate in mammals and especially in humans conditions such as hypertension, peripheral vascular disease, high blood pressure, and coronary artery disease.

In general, the following methods for assay of activity were as described previously or cited in Proceedings of the National Academy of Sciences [PNAS], vol. 96, pp. 14136–14142 (1999).

Neurobehavioral Effects

Tail Flick Assay

The protocol of the tail-flick test was as follows. The apparatus that was used for the tail-flick test contained a light source placed directly above a photocell connected to a timer. The mouse was held under a cloth by the technician conducting the experiment. The tail of the test animal was placed over the photocell and the light was turned on. When the test animal felt the discomfort of the heat from the light, it was freely able to remove its tail from the lamp. The photocell than sensed that the tail had moved and the timer was stopped. The typical nontreatment reaction time for an animal subjected to this test was about 2–4 seconds. This test involved a spinal reflex action similar to the removal of a finger from a hot stove. In treated animals, the latency to remove the tail lengthens in proportion to the analgesic potency of the drug. No animal was allowed to remain under the lamp for greater than 10 seconds to prevent any burns to the tail. No animal was subjected twice to this test.

Locomotor activity, ring immobility, and core body temperature parameters were measured as described in detail by Smith et al. (*J. Pharmacol. Exp.Ther.* (1994) 270; 219–227). Briefly, spontaneous locomotor activity is expressed as % inhibition vs. control. Mice were placed in individual activity cages 5 minutes post treatment, and interruption of the photocell beams (16 beams/chamber) were recorded for a 10 minute period using a Digiscan Animal Activity Monitor (Omnitech). Core temperature was measured by a rectal thermistor inserted to 25 mm, before and 30 minutes after administration of Abn-cbd. Catalepsy (ring immobility procedure) was expressed as % of total time spent motionless. Test compound can be injected into a tail vain i.v., and measurements are performed at 5 min (spontaneous motility), min (tail flick latency), 60 min (Core temperature) or 90 min (ring immobility) after drug injection. None of the values is significantly different from the corresponding drug-free control value.

Animals

Adult ICR mice (25–30 g) were from Harlan (Indianapolis, Ind.). Both male and female animals were used for these studies. Animals were housed four at a cage with standard mouse chow and water ad libitum, and were maintained at 24–261C under a 12:12 light:dark cycle.

Radioligand Binding

3H-CP-55,940 binding to P2 membranes from rat brain was conducted as described elsewhere (*J. Pharmacol. Exp.Ther.* (1993) 265; 218–226). In saturation experiments (n–5), the b=., (1.2±0.2 pmoUmg protein) and KI) values (809±21 pM) were similar to published values.

Cardiovascular Measurements

The effects of cannabinoids on blood pressure were performed in anesthetized rather than conscious mice, as anesthesia was found to potentiate the $CB_1$ receptor-mediated hypotensive effect of anandamide (Lake et al. (1997) *Hypertension* 29, 1204–1210). Male and female mice (25–30 g) were anesthetized with sodium pentobarbital, 60 mg/kg i.p., and PE10 cannulae were inserted into the carotid artery and jugular vein for continuous monitoring of blood pressure and heart rate and for injecting drugs, respectively. Drugs were injected as bolus i.v. doses in volumes $\leq 550\,\mu l$. Injection of vehicle caused no significant change in blood pressure.

For measuring drug effects on mesenteric vascular tone in mice, sodium pentobarbital-anesthetized mice were laparotornized and a PE50 cannula was inserted distally into the abdominal aorta. Both renal and both femoral arteries were ligated, the heart removed, and the mesenteric area including the liver was perfused with oxygenated Krebs buffer at 36° C., using a peristaltic pump and a constant flow rate of 0.7 ml/min. Perfusion pressure monitored close to the inflow cannula was 25–30 mmHg, and was increased to 60–70 mmHg by the inclusion of 15 $\mu M$ phenylephrine in the medium. Vasodilator effects were expressed as % relaxation of established tone, 100% being equal to the difference in perfusion pressure in the absence and presence of phenylephrine.

The methods used to analyze drug effects on vascular tone in the rat isolated mesenteric arterial bed and to achieve endothelial denudation by brief perfusion with distilled water have been described in detail elsewhere (Wagner et al.(1999), *Hypertension* 33 (Part II), 429–434). Because of the long lasting vasodilator effect of anandamide, R-methanandamide and abnormal cannabidiol, each preparation was tested with a single dose of the agonist, either in the absence or the presence of an antagonist.

COMPOUNDS

The derivatives of cannabidiol and Abn-cbd are synthesized using techniques that are well known in the relevant art. The modified compounds in general have changes in the pentyl side chain or additions of halogens to the orcinol ring.

In general, to synthesize the compounds of the present invention, the corresponding resourcinol is condensed in the presence of "compound I" with a mild acid added as catalyst and subjected to reflux for approximately four hours (Razdan, et al. (1974) *J. Am. Chem. Soc.* 96: 5860–5865; T. Petrzilka et al. (1969) *Helv. Chimica Acta*, 52:1102). Purity is established by nuclear magnetic resonance spectroscopy, gas chromatography and elemental analysis By way of example, the Abn-cbd antagonist 0-1847 is synthesized as follows:

Compound 1          Compound II

To a mixture of approximately 0.76 g compound 1 (5 mmol) and approximately 0.71 g compound II (5 mmol) is added 15 ml ether to dissolve the orcinol followed by the addition of 35 ml benzene. To this mixture approximately 0.756 g (6 mmol) oxalic acid.$2H_2O$ is added and the mixture is then stirred under $N_2$ at 80° C. (Oil bath) for approximately 4–5 hours as described previously for the synthesis of Abn-cbd. After 5 hours, the mixture is cooled, approximately 20 ml ether is added and the mixture is then reacted with 1X $NaHCO_3$ solution to remove the acid. The reaction mixture is then washed sequentially with approximately 30 ml $H_2O$, 30 ml brine, dried and evaporated to yield a gum/syrup material. The product is then purified for example, by flash chromatography on approximately 70 g $SiO_2$, in 7% EtAc/Hexane and eluted with approximately 400 ml Et/Ac Hexane followed by 1 liter of 14% EtAc/Hexane.

By way of further example, compound 0-1602 is synthesized as follows:

Compound 1          Compound II

-continued

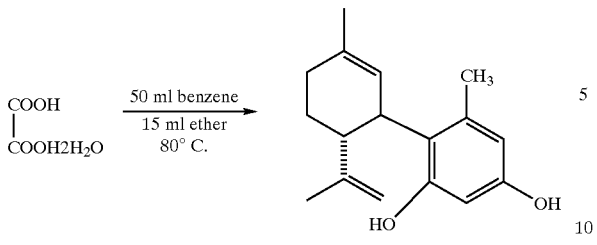

To a mixture of approximately 0.76 g compound 1 (5 mmol) and approximately 0.71 g compound II (5 mmol) is added approximately 50 ml benzene and 15 ml ether to dissolve the orcinol. To this mixture approximately 0.756 g (6 mmol) oxalic acid.$2H_2O$ is added and the mixture is then stirred under $N_2$ at 80° C. (Oil bath) as described previously for the synthesis of Abn-cbd. After 5 hours, the mixture is cooled, approximately 20 ml ether is added and the mixture is then reacted with 1X $NaHCO_3$ solution to remove the acid. The reaction mixture is then washed sequentially with approximately 30 ml $H_2O$, 30 ml brine, dried and evaporated to yield a gum/syrup material. The product is then purified for example, by chromatography on approximately 60 g $SiO_2$ in 7% EtAc/Hexane and eluted with approximately 400 ml 7% Et/Ac Hexane followed by 1 liter of 14% EtAc/Hexane.

By way of further example, compound 0-1868 is synthesized following reduction of the pentyl side chain of cannabinoid to a methyl group to yield the compound "0-1821": (−)-2-(3-3,4-trans-p-menthadien-(1,8)-orcinol. This product was reacted with KI+18-Crown6+MCPBA under nitrogen. In a round bottom flask was placed 25.8 mg of 0-1821 which was then dissolved in 0.35 ml of methylene chloride. Finely powdered KI (132 mg, 0.5 mmol) was added with stirring followed by, 1.66 mg (0.01 mmol) of 18-Crown6 and continued stirring for another 10 min. To this mixture was added a solution of 25.8 mg (0.012 mmol) of m-chloroperbenzoic acid (MCPBA; 77% pure; Aldrich Chemical Co.). In 0.2 ml methylene chloride over 2–3 min. Continued stirring vigorously for an additional 15 min. The reaction was then quenched by the addition of 5 ml of ether. The solution was washed with 10% sodium bisulphite solution, followed by saturated sodium bicarbonate solution and 2× brine, dried and concentrated on the rotavap to leave an oil. It was purified by preparative TLC using a baker silica 250F plate, eluting with 20% ethyl acetate/hexane to give 0.009 mg (18%) of the compound 0-1868((−)-2-(3-3,4-trans-p-menthadien-(1,8)-4,6-diiodoorcinol). $^1$HNMR ($CDCl_3$) δ, 1.68–1.55 (m, 4H), 1.80 (br 5, 6H), 2.50–2.11 (m, 3H), 2.78 (s, 3H), 4.08 (m, 1H), 4.38 (d,]=2 Hz, 1H), 4.54 (d,]=2 Hz, 1H), 5.48 (br s, 1H). Anal Calcd. for $C_{17}H_{20}I_2O_2$: C, 40.02; H, 3.95; Found: C, 39.92; H, 4.01.

Cannabinoids and derivative compounds for administration were dissolved in Alkmulphor/ethanol/saline 1:1:18. Cannabidiol has the chemical structure

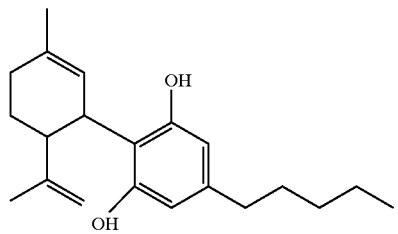

Derivatives of the normal cannabidiol that are encompassed by the present invention have the general formula

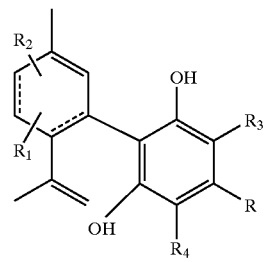

wherein the dashed line represents either a single or double bond, R=H, or $(CH_2)nCH_3$, wherein n=0–9, $R_1$ and $R_2$=H, a lower alkyl (e.g., $C_{1-12}$ alkyl), or a branched alkyl, and $R_3$ and $R_4$=H, I, Cl, Br, or F.

The compounds of the present invention include derivatives of cannabidiol, which are candidates, for an antagonistic effect on Abn-cbd-induced vasodilation.

In one preferred embodiment, the invention provides the compound designated as "0-1821", wherein the pentyl side chain of cannabidiol is replaced by a methyl group. The compound 0-1821 thus has the chemical formula

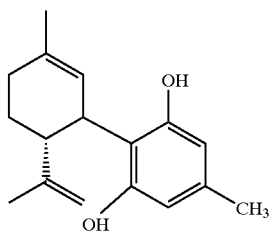

The 0-1821 compound does not elicit a response in the tetrad of standard neurobehavioral effects described supra (30 μg/kg). The 0-1821 compound showed no significant binding to CB1 receptors at a concentration of 10 μM. The 0-1821 compound did not elicit vasodilation when injected intraarterially as a 1 mg bolus. Results of vasodilation as shown in FIG. 2(A) demonstrate further that 0-1821 causes a dose-dependent pronounced inhibition of Abn-cbd analog (0-1602)-induced vasodilation.

In another preferred embodiment, the invention provides the compound designated as "0-1847", wherein the pentyl side chain of cannabidiol is replaced by a hydrogen atom. The compound 0-1847 thus has the chemical formula

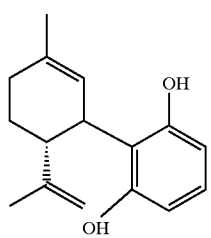

The 0-1847 compound does not elicit a response in the tetrad of standard neurobehavioral effects described supra (30 μg/kg). The 0-1847 compound showed no significant binding to CB1 receptors at a concentration of 10 μM. The 0-1847 compound did not elicit mesenteric vasodilation when injected intraarterially as a 1 mg bolus. Results of vasodilation as shown in FIG. 2(B) demonstrate further that 0-1847 causes a dose-dependent pronounced inhibition of Abn-cbd analog (0-1848)-induced vasodilation.

In another preferred embodiment, the invention provides the compound designated as "O-1868", wherein the pentyl side chain of cannabidiol is replaced by a methyl group and R3 and R4 are Iodine. The compound O-1868 thus has the chemical formula

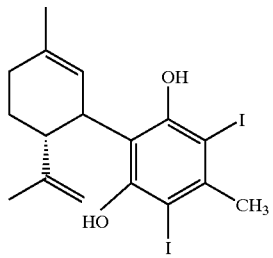

The O-1868 compound does not elicit a response in the tetrad of standard neurobehavioral effects described supra (30 μg/kg). The O-1868 compound showed no significant binding to CB1 receptors at a concentration of 10 μM. The O-1868 compound did not elicit mesenteric vasodilation when injected intraarterially as a 1 mg bolus. Results of vasodilation as shown in FIG. 2(C) demonstrate further that O-1868 causes a dose-dependent pronounced inhibition of Abn-cbd analog (O-1848)-induced vasodilation.

Abnormal cannabidiol, (–)-4-(3-3,4-trans-p-menthadien-1,8)-yl-olivetol results from the transposition of the phenolic hydroxyl group and the pentyl side chain of cannabidiol. It was synthesized as described previously (Razdan, et al. (1974) *J. Am. Chem. Soc.* 96: 5860–5865), and its purity was established by nuclear magnetic resonance spectroscopy, gas chromatography and elemental analysis. The compounds of the present invention include derivatives of Abn-cbd, which are candidates for an agonistic effect on Abn-cbd vasodilation. Abnormal cannabidiol (Abn-cbd) has the chemical structure

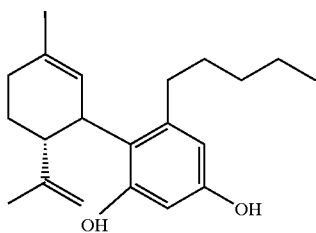

In general terms, derivatives of abnormal cannabidiol as contemplated by the present invention can have the formula

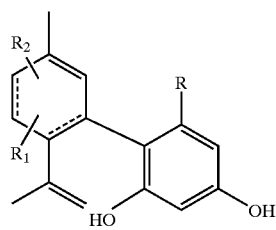

wherein the dashed lines depict single or double bonds, R=H or $(CH_2)_nCH_3$ wherein n=0–9 and $R_1$ and $R_2$=H, a lower alkyl group or a branched alkyl group.

In one preferred embodiment, the invention provides the compound designated as "O-1602", wherein the pentyl side chain of Abn-cbd is replaced by a methyl group. The compound O-1602 thus has the chemical formula

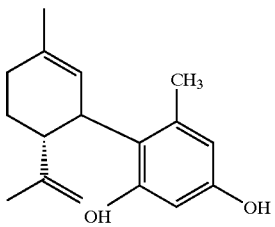

The O-1602 compound does not elicit a response in the tetrad of standard neurobehavioral effects described supra. Results of vasodilation as shown in FIG. 1 demonstrate further that O-1602 causes a dose-dependent pronounced vasodilation at 80× lower doses than the doses of Abn-cbd required to produce similar effects. Vasodilation induced by O-1602 (54%±2% at 100 μg, n=4) was markedly reduced in the presence of SR141716A (15%±3%, n=3, P<0.005) or after endothelial denudation (18%±2%, n=3, P<0.005).

In another preferred embodiment, the invention provides the compound designated as "O-1848," wherein the pentyl side chain of Abn-cbd is replaced by a hydrogen atom. The compound O-1848 thus has the chemical formula

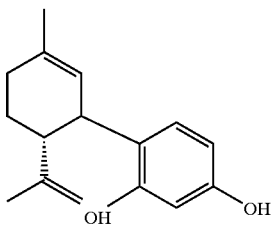

The O-1848 compound does not elicit a response in the tetrad of standard neurobehavioral effects described supra. Results of vasodilation as shown in FIG. 2 demonstrate further that O-1848 causes a dose-dependent pronounced vasodilation at 80× lower doses than Abn-cbd. Furthermore, O-1848 elicits a hypotensive effect in urethane-anaesthetized spontaneous hypertensive (SHR) rats. Repeatable (5 animals) reductions in mean blood pressure were observed.

The invention further provides a method of using these compounds as agonists, or as antagonists. The compounds of the invention can be used either as the free base or as the pharmaceutically acceptable acid-addition salt form, for example, hydrochloride, hydrobromide, hydrobromide, tatrate, and maleate. They may be used in oral or injectable pharmaceutical preparations as prophylactic and acute-phase remedies for the relief and reversal of excessive vasoconstriction or vasodilation. They may be used alone or in combination with each other or other known medications. Finally, said compounds may be used as above for determining non-CB1 and non CB2 receptor function.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The compounds described herein in the practice of the inventive therapeutic method can be administered via aerosol delivery via an atomized aqueous medium.

The administration of pharmaceutical compositions of the present invention can be intermittent, or at a gradual, or continuous, constant or controlled rate to a warm-blooded animal. In addition, the time of day and the number of times per day that the pharmaceutical formulation is administered can vary.

The effective dose can vary, depending upon factors such as the condition, size and age of the patient, the severity of the symptoms being treated, and the manner in which the pharmaceutical composition is administered. For human patients, preferably, the dosage is divided up into several equal smaller dosages administered at regular time intervals over each 24 hr. period. The oral administration can be accomplished using aqueous pharmacological solutions, suspensions, emulsions, syrups, elixirs, and so forth, which have the THC derivative active agents solubilized therein. The pharmaceutical compositions of the present invention comprise derivatives of cannabidiol or Abn-cbd that have as an active ingredient or a pharmaceutically acceptable salt, thereof, and may also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The apparent selectivity of cannabidiol and its derivatives as antagonists and the indications of a structure-activity relationship for Abn-cbd and its analogs 0-1602 and 0-1848 strongly suggest that the site of action of these compounds is a receptor.

EXAMPLES

Example I

FIG. 1 shows the results of the vasodilator effect of 0-1602 (open circles, 0-1848 (closed circles) and Abn-cbd (squares). These results demonstrate the agonistic effect of 0-1602 and 0-1848 on the effects of Abn-cbd. These procedures were done as described previously in PNAS 96, pp. 14136–14142 (1999). Mice were anesthetized with pentobarbitol and laparotomized and cannulated using a PE50 polyethylene cannula inserted into the abdominal aorta. Both renal and femoral arteries were ligated, the heart was removed, and the mesenteric area including the liver was perfused with oxygenated Krebs buffer at 36° C., using a peristaltic pump and a constant flow rate of 0.7 ml/min. Perfusion pressure monitored near the inflow cannula should be 25–30 mmHg (1 mmHg+133 Pa) and is increased to 60–70 mmHg by the inclusion of 15 mM phenylephrine in the medium. Vasodilation is expressed as percent relaxation of established tone, 100% being equal to the difference in perfusion pressure in the absence and presence of phenylephrine. The X-axis shows the effects of different doses of the various compounds injected as an intra arterial bolus.

Example II

FIG. 2 shows the results of inhibition of 0-1602 or 0-1848 induced vasodilation following treatment with cannabinoid analogs. These results demonstrate that 0-1821, 0-1847, and 0-1868 are antagonists of the Abn-cbd derivatives described herein. Evaluation of vasodilator response was performed as in Example 1 except that after addition of either the agonists 0-1602 (FIG. 2A) or 0-1848 (FIG. 2B–2C) as intra arterial bolus injections, the mesenteric preparation was perfused with either drug free buffer (solid circles) or buffer containing 1 $\mu$M. 0-1821 (FIG. 2(A), open circles), 0-1847 (FIG. 2(B), open circles), or 0-1868 (FIG. 2(C), open circles. The shaded circles in FIG. 2(A) represent the antagonistic effect of 0-1821 at a concentration of 10 $\mu$M, a concentration which shows almost complete inhibition of the vasodilatory effect of compound 0-1602. This figure demonstrates the antagonist effects of the cannabidiol derivatives of the present invention.

While the invention has been described in terms of a single preferred embodiment, those skilled in the art will recognize that the invention can be practiced with modification within the spirit and scope of the appended claims.

What is claimed is:

1. A compound having the chemical structure:

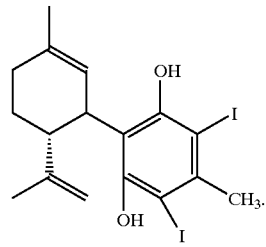

2. A method for the treatment of a pathological state involving excessive vasoconstruction or vasodilation coprising administering to a patient a therapeutic amount of an agonist or an antagonist having a chemical structure selected from the group consisting of:

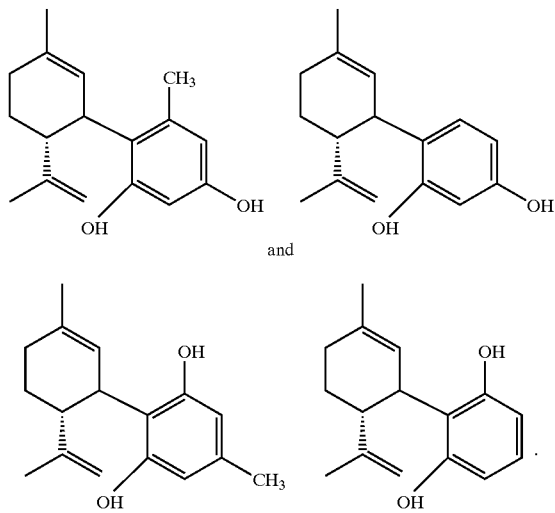

3. A method for the treatment of a pathological state causing abnormal blood pressure or heart rate comprising administering to a patient a therapeutic amount of an agonist or an antagonist having a chemical structure selected from the group consisting of:

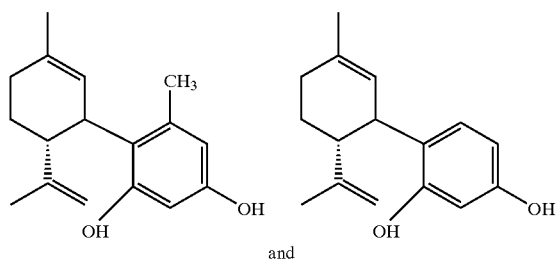

and

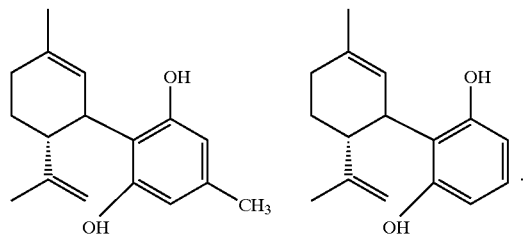

4. The method of claim 2 wherein the chemical structure is

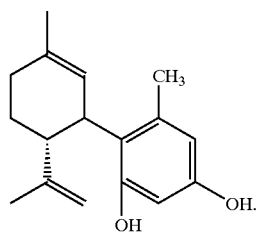

5. The method of claim 3 wherein the chemical structure is

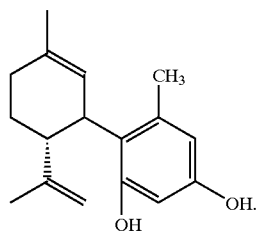

6. The method of claim 2 wherein the chemical structure is

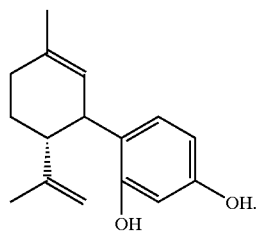

7. The method of claim 3 wherein the chemical structure is

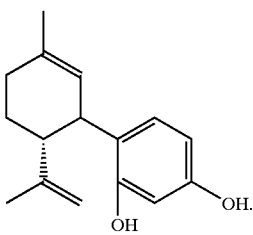

8. The method of claim 2 wherein the chemical structure is

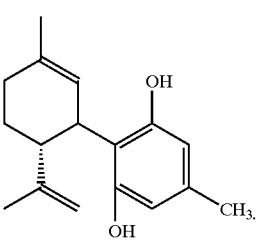

9. The method of claim 2 wherein the chemical structure is

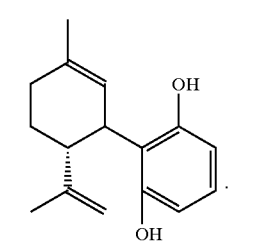

10. The method of claim 3 wherein the chemical structure is

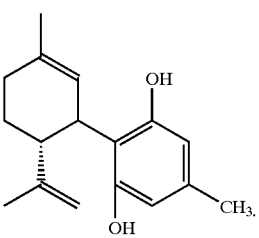

11. The method of claim 3 wherein the chemical structure is

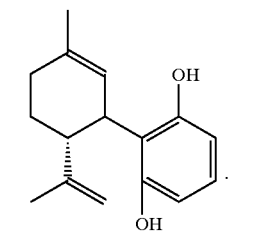

* * * * *

UNITED STATES PATENT AND TRADEMARK OFFICE
CERTIFICATE OF CORRECTION

| | | |
|---|---|---|
| PATENT NO. | : 6,563,009 B1 | |
| APPLICATION NO. | : 10/009813 | |
| DATED | : May 13, 2003 | |
| INVENTOR(S) | : George Kunos, Billy Martin and Raj Razdan | |

It is certified that error appears in the above-identified patent and that said Letters Patent is hereby corrected as shown below:

In the Specification

At Column 1, line 7, please insert the following:

--STATEMENT OF GOVERNMENT INTEREST

This invention was made with government support under contract number HL052597 awarded by the National Institutes of Health. The government has certain rights in the invention.--

Signed and Sealed this
Twenty-third Day of December, 2014

Michelle K. Lee
*Deputy Director of the United States Patent and Trademark Office*